United States Patent [19]

Huettinger et al.

[11] Patent Number: 4,614,622
[45] Date of Patent: Sep. 30, 1986

[54] POLYOXYALKYLENE ETHERS OF GLYCERIN OR 1,2-PROPANEDIOL, ESTERIFIED WITH FATTY ACID AND/OR ISOSTEARIC ACID, THEIR SYNTHESIS AND USE AS THICKENING OR SOLUBILIZING AGENTS

[75] Inventors: Rüdolf Huettinger; Ulrich Holtschmidt, both of Essen, Fed. Rep. of Germany

[73] Assignee: Th. Goldschmidt AG, Essen, Fed. Rep. of Germany

[21] Appl. No.: 544,616

[22] Filed: Oct. 24, 1983

[30] Foreign Application Priority Data

Oct. 26, 1982 [DE] Fed. Rep. of Germany ....... 3239564

[51] Int. Cl.⁴ .............................................. C11C 3/02
[52] U.S. Cl. .............................. 260/410.7; 260/410.6
[58] Field of Search ............... 260/410.7, 410.6, 410.8; 424/307

[56] References Cited

U.S. PATENT DOCUMENTS

| | | | |
|---|---|---|---|
| 2,307,495 | 1/1943 | De Groote et al. | 260/410.7 |
| 2,542,550 | 2/1951 | McDermott | 260/410.7 |
| 3,066,159 | 11/1962 | De Groote et al. | 260/410.7 X |
| 3,312,542 | 4/1967 | Kitzke | 260/410.7 X |
| 3,337,595 | 8/1967 | Lamont | 260/410.7 X |
| 3,433,645 | 3/1969 | Egan et al. | 260/410.7 |
| 3,435,024 | 3/1969 | Nobile et al. | 260/410.7 X |
| 3,663,583 | 5/1972 | Haynes | 260/410.7 |
| 3,691,219 | 9/1972 | Boussely | 260/410.7 |
| 3,720,695 | 3/1973 | Meisters | 260/410.7 X |
| 3,799,958 | 3/1974 | Mitchell | 260/410.7 |

FOREIGN PATENT DOCUMENTS

1270542  6/1968  Fed. Rep. of Germany ... 260/410.7

OTHER PUBLICATIONS

Chemical Abstracts, 99, 89590g (1983).
Chemical Abstracts, 95, 64170z (1981).
Chemical Abstracts, 96, 11502y (1982).
Chemical Abstracts, 95, 188185c (1981).
Chemical Abstracts, 97, 714p (1982).

*Primary Examiner*—Helen M. S. Sneed
*Attorney, Agent, or Firm*—Toren, McGeady, Stanger, Goldberg & Kiel

[57] ABSTRACT

Compounds having the formula:

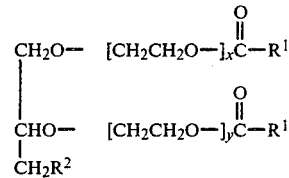

in which $R^1$ is the hydrocarbon radical of a fatty acid with 16 to 18 carbon atoms, isostearic acid or a mixture thereof, $R^2$ is hydrogen or the

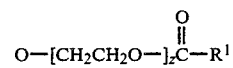

radical,
x y and z are whole numbers
and the sum of $x+y+z$ has a value from 50 to 60.

The invention furthermore relates to the synthesis of these compounds as well as to the use of these compounds as thickening agents, especially for aqueous, surfactant-containing solutions and as solubilizing agents, especially for cosmetic preparations.

4 Claims, No Drawings

POLYOXYALKYLENE ETHERS OF GLYCERIN OR 1,2-PROPANEDIOL, ESTERIFIED WITH FATTY ACID AND/OR ISOSTEARIC ACID, THEIR SYNTHESIS AND USE AS THICKENING OR SOLUBILIZING AGENTS

BACKGROUND OF THE INVENTION

1. Field of the Invention

This invention relates to aqueous cosmetic and pharmaceutical preparations as well as additives therefor.

2. Description of the Prior Art

Aqueous preparations of active ingredients are frequently used in pharmaceutics and especially in cosmetics. For reasons related to the application or use of the preparations, it may be desirable that the preparations have an increased viscosity and exist in the form of gels or pastes.

Typical examples of such cosmetic preparations are highly viscous or gel-like shampoos as well as bath and shower gels. Besides active cosmetic ingredients, these products contain surfactants, especially anionic surfactants, such as, for example, alkylbenzene sulfonates and alkyl ether sulfates. Also, in recent years, betaines have been used to an increasing extent as surfactants.

Until now, anionic or cationic, synthetic polymers or vegetable thickening agents have been used to thicken such preparations. It is however a disadvantage of these known thickening agents that they cannot be universally employed, but are system-specific and frequently produce cloudiness and form deposits. Such products are especially unsuitable for thickening aqueous betaine solutions.

Salts, such as, for example, sodium chloride, have been added to anionic surfactants. This addition is ineffective with sulfosuccinic esters and betaines. Moreover, in larger quantities, the added mineral salts have a salting out effect on the dissolved surfactants and detract from the ability of such solutions to have a solubilizing effect.

Polyethyleneglycol derivatives which act as thickeners are disclosed in German Offenlegungsschrift No. 31 40 160. These compounds correspond to the general formula:

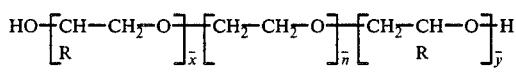

in which
R represents an alkyl radical and/or an alkoxymethyl radical or a mixture of these radicals;
$\bar{n}$ represents an average group number of 20 to 500 and, preferably, of 30 to 200, and
$\bar{x}$ and $\bar{y}$ represent average group numbers of 0 to 8, the sum $(\bar{x}+\bar{y})$ varying between 1 and 8.

These compounds are synthesized by adding long chain 1,2-alkylene oxides, such as, for example, 1,2-octadecene oxides or alkyl glycidyl ethers, such as, for example oleyl glycidyl or alkenyl glycidyl ethers, to polyethylene glycols.

The compounds of the above-mentioned Offenlegungsschrift are relatively expensive because of the long-chain epoxides used. Moreover, their thickening capability and especially their solubilizing capability are not always adequate.

SUMMARY OF THE INVENTION

We have discovered compounds which can be synthesized from readily accessible raw materials, have excellent thickening properties, and moreover, are capable of solubilizing active ingredients, such as, for example, essential oils.

More particularly, we have discovered that these properties are found in compounds having the general formula:

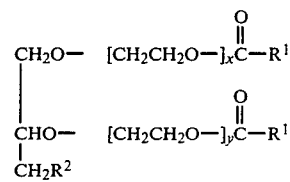

in which $R^1$ is the hydrocarbon radical of a fatty acid with 16 to 18 carbon atoms, isostearic acid, or a mixture thereof, $R^2$ is hydrogen or the

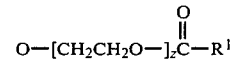

radical, x, y and z are whole numbers and the sum of $x+y+z$ has a value of from 50 to 60.

DESCRIPTION OF THE PREFERRED EMBODIMENT

The thickening properties of these compounds become considerably inferior if the sum of $x+y+y$ falls below the value of 50 or exceeds the value of 60. It was unexpected that compounds with particularly advantageous thickening properties for aqueous solutions, especially for surfactants, are to be found within the range selected.

Compounds in which $R^1$ is completely or predominantly the oleyl radical are particularly preferred. Compounds in which $R^1$ is completely or predominantly the stearyl radical also have good thickening properties, however, the solubility of these compounds in aqueous systems is less than that of the corresponding oleyl derivatives.

Especially preferred are compounds in which $R^1$ is the oleyl radical and $R^2$ is a hydrogen radical.

German Auslegeschrift No. 20 24 051 discloses the use of esterification products of ethylene oxide-glycerin addition compounds having 4 to 20 moles of ethylene oxide per mole of glycerin, with fatty acids having a chain length of 8 to 18 carbon atoms, in a ratio of 1 to 2 moles of fatty acid to 1 mole of glycerin/ethylene oxide addition product as refatting agent in cosmetic preparations and especially cosmetic cleansing agents.

These compounds, however, differ from the inventive compound in their ethylene oxide content and by having a lesser degree of esterification. These materials do not have a thickening effect in aqueous surfactant solutions and, therefore, could not suggest the object of the present invention.

In a further development of the invention, the inventive compounds are synthesized by adding 50 to 60 moles of ethylene oxide to glycerin or 1,2-propanediol in the presence of conventional catalysts at temperatures of 80° to 150° C. and at elevated pressure, and esterifying, transesterifying or reacting the addition product at elevated temperatures with at least equivalent amounts, based on the hydroxyl groups, of $R^1COOH$, $R^1COOCH_3$ or $R^1COCl$, respectively, and removing the water or methanol or neutralizing the hydrogen chloride released during the reaction.

The addition of ethylene oxide to glycerin or 1,2-propanediol is a reaction which has long been known and is carried out in the inventive process by a known procedure. The addition takes place in an autoclave in the presence of the usual catalysts, such as, for example, slight amounts of alkali methylate, and at elevated temperatures of 80° to 150° C. and an elevated pressure.

The ester is then prepared from this addition product by a known procedure. Processes known from the state of the art can be used for this purpose.

For example, the addition product can be esterified directly with the carboxylic acid or the carboxylic acid mixture, advisably in the presence of an esterification catalyst, such as, for example, small amounts of alkali hydroxide or n-butyl titanate, with removal of the water of reaction.

It is, of course, also possible to transesterify the addition product with the appropriate methyl ester of the carboxylic acid with removal of the methanol formed.

It is furthermore possible to react the addition product with appropriate acid chlorides and to neutralize the hydrogen chloride released. In this case, it is advisable to remove the chloride formed in order to prevent its salting out effect in the preparations.

The reaction of the polyethyleneglycol addition product with the carboxylic acid or its mixture or derivatives is carried out in amounts, such that, preferably, all hydroxyl groups of the addition product are reacted. Therefore, the addition product is reacted with at least equivalent amounts, based on the hydroxyl groups, of carboxylic acid(s) or its (their) derivatives. The inventive compounds are solid, waxy substances.

Surprisingly, it turned out that the inventive compounds are not only excellent thickening agents, but also have very good solubilizing properties. Moreover, a synergistic effect is frequently to be observed so that larger amounts of, for example, essential oils can be solubilized than is the case when anionic surfactants and the inventive compounds are used separately. The synergistic solubilizing effect is shown especially in conjunction with betaines and is particularly desirable, for example, in the preparation of hair shampoos and bath gels.

The inventive compounds can be used for thickening water-based pharmaceutical and cosmetic preparations. Their preferred area of application comprises thickening aqueous cosmetic preparations, which contain surface active substances, especially anionic substances or betaines.

The synthesis of the inventive compounds and their application properties are described in greater detail in the following examples.

EXAMPLE 1

The product (2292 g) of the addition of 50 moles of ethylene oxide to glycerin (1 mole) is mixed with 882 g of oleic acid (3.15 moles) and esterified in a stream of nitrogen with stirring for 5 hours at 240°-260° C.

EXAMPLE 2

The product (2512 g) of the addition of 55 moles of ethylene oxide to glycerin (1 mole) is mixed with 924 g of oleic acid (3.3 moles) and esterified in a stream of nitrogen with stirring for 5 hours at 240°-260° C.

EXAMPLE 3

The product (2512 g) of the addition of 55 moles of ethylene oxide to glycerin (1 mole) is mixed with 980 g of isostearic acid (3.5 moles) and esterified in a stream of nitrogen with stirring for 5 hours at 240°-260° C.

EXAMPLE 4

The product (2276 g) of the addition of 50 moles of ethylene oxide to 1,2-propanediol (1 mole) is mixed with 840 g of oleic acid (3 moles) and esterified in a stream of nitrogen with stirring for 5 hours at 240°-260° C.

EXAMPLE 5

The product (2540 g) of the addition of 56 moles of ethylene oxide to 1,2-propanediol (1 mole) is mixed with 700 g of oleic acid (2.5 moles) and esterified in a stream of nitrogen with stirring for 5 hours at 240°-260° C.

EXAMPLE 6

The product (2496 g) of the addition of 55 moles of ethylene oxide to 1,2-propanediol (1 mole) is heated with stirring to 100° C. under vacuum. Oleyl chloride (650 g, 2.2 moles) is added in portions within 30 minutes. The reaction is allowed to continue for a further hour until the hydrogen chloride formed has been drawn off quantitatively under vacuum.

EXAMPLE 7

The product (2650 g) of the addition of 55 moles of ethylene oxide to 1,2-propanediol (1.06 mole) is mixed at 100° C. with 590 g of methyl oleate (2 moles). n-Butyl titanate (8-16 g, 0.25-0.50%) is then added as catalyst and the mixture is heated under vacuum with stirring for 4 to 6 hours at 80°-200° C.

EXAMPLE 8

The product (2496 g) of the addition of 55 moles of ethylene oxide to 1,2-propanediol (1 mole) is mixed at 100° C. with 588 g of oleic acid (2.1 moles). n-Butyl titanate (12 g, 0.4%) is then added and the mixture is heated under vacuum with stirring for 6 hours at 200°-220° C.

EXAMPLE 9

The product (2276 g) of the addition of 50 moles of ethylene oxide to 1,2-propanediol (1 mole) is mixed at 100° C. with 640 g of a palmitic/stearic acid mixture (2.4 moles). n-Butyl titanate (7.2 g, 0.25%) is then added and the mixture is heated under vacuum with stirring for 6 hours at 200°-220° C.

Table 1 shows the excellent solubilizing properties of the inventive compounds and the observed synergistic effect.

Table 2 shows the outstanding thickening properties of the inventive compounds.

The surfactants used have the following chemical composition:
betaine 1—1-alkoylamino-3-dimethylammoniopropane-3-carboxymethylbetaine
betaine 4—lauryl dimethylglycine
anionic surfactant 2—sodium lauryl ether sulfate
anionic surfactant 5—lauryl alcohol polyglycol ether sulfosuccinate, sodium salt anionic surfactant 3—triethanolamine lauryl sulfate
cationic surfactant 10—stearyl pentaoxyethylammonium chloride
nonionic surfactant 7—polyoxyethylene(7)lauryl ether
nonionic surfactant 8—polyoxyethylene(10)nonylphenol ether
nonionic surfactant 9—1-alkoylamino-3-dimethylaminopropane-3-N-oxide The viscosities were measured with a Hoeppler falling ball viscosimeter at 20° C.

TABLE 1
SOLUBILIZING (all data in g/100 g of solution)

| Product of the Invention Example 8 | Betaine 1 | Anionic Surfactant 1 | Anionic Surfactant 3 | Water | Solubilized Amount | Perfume |
|---|---|---|---|---|---|---|
| 10 | | | | 89.0 | 1.0 | menthol |
| | 6 | | | 79.0 | 1.0 | |
| 10 | 6 | | | 66.0 | 4.0 | |
| 10 | | | | 89.5 | 0.5 | peppermint oil |
| | 6 | | | 79.0 | 1.0 | |
| 10 | 6 | | | 66.0 | 4.0 | |
| 10 | | | | 89.5 | 0.5 | eucalyptus oil |
| | 6 | | | 79.0 | 1.0 | |
| 10 | 6 | | | 66.0 | 4.0 | |
| | | 5.6 | | 77.0 | 3.0 | |
| 10 | | 5.6 | | 66.0 | 4.0 | |
| | | | 6 | 77.0 | 3.0 | |
| 10 | | | 6 | 66.5 | 3.5 | |
| 10 | | | | 89.8 | 0.2 | pine needle oil |
| | 6 | | | 79.5 | 0.5 | |
| 10 | 6 | | | 65.0 | 5.0 | |
| | | 5.6 | | 79.0 | 1.0 | |
| 10 | | 5.6 | | 66.5 | 3.5 | |
| | | | 6 | 79.0 | 1.0 | |
| 10 | | | 6 | 67.5 | 2.5 | |

TABLE 2
TICKENING OF SURFACTANT SOLUTIONS

| Product from Example | g/100 g | Surfactant | g/100 g Solution | Water g/100 g Solution | Viscosity mPas |
|---|---|---|---|---|---|
| 1 | 7.5 | betaine 1 | 7.5 | 85.0 | 15 000 |
| 2 | 7.5 | betaine 1 | 7.5 | 85.0 | 4 000 |
| 3 | 7.5 | betaine 1 | 7.5 | 8.50 | 15 000 |
| 4 | 5.0 | betaine 1 | 7.5 | 87.5 | 9 000 |
| 5 | 5.0 | betaine 1 | 7.5 | 87.5 | 12 000 |
| 6 | 5.0 | betaine 1 | 7.5 | 87.5 | 40 000 |
| 7 | 5.0 | betaine 1 | 7.5 | 87.5 | 30 000 |
| 8 | 5.0 | betaine 1 | 7.5 | 87.5 | 28 000 |
| 9 | 5.0 | betaine 1 | 7.5 | 87.5 | 20 000 |
| 8 | 5.0 | betaine 4 | 6.25 | 88.75 | 15 000 |
| 8 | 5.0 | anionic surfactant 5 | 6.25 | 88.75 | 10 000 |
| 8 | 5.0 | anionic surfactant 6 | 6.25 | 88.75 | 30 000 |
| 8 | 5.0 | nonionic surfactant 7 | 6.25 | 88.75 | 4 000 |
| 8 | 5.0 | nonionic surfactant 8 | 6.25 | 88.75 | 4 000 |
| 8 | 5.0 | nonionic surfactant 9 | 6.25 | 88.75 | 15 000 |
| 8 | 5.0 | cationic surfactant 10 | 6.25 | 88.75 | 7 000 |

We claim:

1. Compounds having the formula:

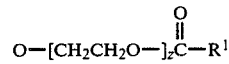

in which $R^1$ is the hydrocarbon radical of a fatty acid with 16 to 18 carbon atoms, isostearic acid, or a mixture thereof, $R^2$ is hydrogen or the $$O-[CH_2CH_2O-]_z\overset{O}{\underset{\|}{C}}-R^1$$

radical, x y and z are whole numbers and the sum of $x+y+z$ has a value from 50 to 60.

2. The compound of claim 1 wherein $R^1$ is predominantly or completely the oleyl radical.

3. The compound of claim 1 wherein $R^1$ is predominantly or completely the stearyl radical.

4. The compound of claim 1 wherein $R^1$ is the oleyl radical and $R^2$ is hydrogen.

* * * * *